(12) United States Patent
Freudenberger et al.

(10) Patent No.: US 12,225,655 B2
(45) Date of Patent: Feb. 11, 2025

(54) X-RAY EMITTER HOUSING WITH AT LEAST ONE ELECTRICALLY CONDUCTIVE HOUSING PORTION

(71) Applicant: Siemens Healthineers AG, Forchheim (DE)

(72) Inventors: Joerg Freudenberger, Kalchreuth (DE); Wolfgang Schaeff, Burgthann (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/358,201

(22) Filed: Jul. 25, 2023

(65) Prior Publication Data
US 2024/0038480 A1 Feb. 1, 2024

(30) Foreign Application Priority Data
Jul. 28, 2022 (EP) .................................... 22187531

(51) Int. Cl.
*H05G 1/70* (2006.01)
*A61B 6/00* (2024.01)
(Continued)

(52) U.S. Cl.
CPC ................ *H05G 1/70* (2013.01); *A61B 6/03* (2013.01); *A61B 6/4007* (2013.01); *H01J 35/16* (2013.01);
(Continued)

(58) Field of Classification Search
CPC . H05G 1/70; H05G 1/025; A61B 6/03; A61B 6/4007; A61B 6/4488; H01J 35/16; H01J 2235/023; H01J 2235/1216
See application file for complete search history.

(56) References Cited

U.S. PATENT DOCUMENTS

| 4,767,961 A | 8/1988 | Koller et al. |
| 5,303,283 A | 4/1994 | Jedlitschka et al. |
(Continued)

FOREIGN PATENT DOCUMENTS

| CA | 370779 A | 12/1937 |
| CN | 102283668 A | 12/2011 |
(Continued)

OTHER PUBLICATIONS

Extended European Search Report for European Application No. 22187531.3 and English translation thereof mailed Jan. 26, 2023.
(Continued)

*Primary Examiner* — Chih-Cheng Kao
(74) *Attorney, Agent, or Firm* — Harness, Dickey & Pierce, P.L.C.

(57) ABSTRACT

A multitube X-ray emitter housing according to the invention includes a housing, a high-voltage supply and a cooling device with an electrically insulating cooling medium. The high-voltage supply has a plurality of high-voltage contacts connected in parallel on a single high-voltage supply lead. A first of at least one side surface of the housing has a first electrically conductive housing portion with a temperature-dependent electrical conductivity. The multitube X-ray emitter housing further includes: a control unit having an interface to receive a measured value representing the electrical conductivity of the first electrically conductive housing portion and to compare the measured value with a threshold value; and a switching device to switch off the high voltage based on the comparison.

20 Claims, 6 Drawing Sheets

(51) Int. Cl.
  *A61B 6/03* (2006.01)
  *A61B 6/40* (2024.01)
  *H01J 35/16* (2006.01)
  *H05G 1/02* (2006.01)

(52) U.S. Cl.
  CPC ............ *H05G 1/025* (2013.01); *A61B 6/4488* (2013.01); *H01J 2235/023* (2013.01); *H01J 2235/1216* (2013.01)

(56) References Cited

U.S. PATENT DOCUMENTS

| | | | |
|---|---|---|---|
| 5,438,605 A * | 8/1995 | Burke | H01J 35/02 378/123 |
| 11,183,357 B2 | 11/2021 | Jafari et al. | |
| 2009/0060141 A1 | 3/2009 | Fritzler et al. | |
| 2011/0075802 A1 | 3/2011 | Beckmann et al. | |
| 2011/0311023 A1 | 12/2011 | Sagoh et al. | |
| 2012/0257710 A1 * | 10/2012 | Funk | A61B 6/4064 378/62 |
| 2014/0211923 A1 | 7/2014 | Chen et al. | |
| 2017/0027046 A1 | 1/2017 | Heidrich et al. | |
| 2022/0208504 A1 * | 6/2022 | Matsuura | H05G 1/70 |
| 2024/0016458 A1 | 1/2024 | Freudenberger et al. | |

FOREIGN PATENT DOCUMENTS

| | | |
|---|---|---|
| CN | 102595754 A | 7/2012 |
| CN | 102647842 A | 8/2012 |
| CN | 104851768 A | 8/2015 |
| CN | 106376166 A | 2/2017 |
| CN | 207781529 U | 8/2018 |
| CN | 109893152 A | 6/2019 |
| CN | 109935509 A | 6/2019 |
| CN | 111031917 A | 4/2020 |
| CN | 213462427 U | 6/2021 |
| DE | 19500733 A1 | 8/1995 |
| DE | 102010043540 A1 | 3/2012 |
| DE | 102013210963 A1 | 12/2014 |
| DE | 102013210967 A1 | 12/2014 |
| DE | 202017104053 U1 | 10/2018 |
| DE | 102017214196 A1 | 2/2019 |
| EP | 3586752 A1 | 1/2020 |
| GB | 631284 A | 10/1949 |
| JP | 2003159242 A | 6/2003 |
| JP | 2009158418 A | 7/2009 |
| JP | 2011243421 A | 12/2011 |
| JP | 2012000386 A | 1/2012 |
| KR | 101150778 B1 | 6/2012 |
| WO | WO 2013131628 A1 | 9/2013 |
| WO | WO 2019034417 A1 | 2/2019 |
| WO | WO 2021249471 A1 | 12/2021 |

OTHER PUBLICATIONS

European Communication under Rule 71(3) for European Application No. 22187531.3 and English translation thereof mailed May 29, 2024.
Wikipedia: "Elektrische Leitfähigkeit"; pp. 1-5.
Zhang Bin et al.: "Design of Cooling Test Platform for Soft X-Ray Diagnosis System"; "Nuclear Electronics & Detection Technology"; Bd. 37; Nr. 2; pp. 113-116; Feb. 28, 2017.
Anburajan M et al.;"Sharma, JK, "Overview of X-Ray Tube Technology"; Biomedical Engineering and Its Applications in Healthcare"; pp. 519-547.
Ren Xiang et al.; "The Effect of Forced Cooling of X-Ray Tube on Focalspot Displacement"; "Vacuum Electronics",; Oct. 25, 2021; pp. 68-72.
Iversen A.H et al:; Corporation, C. and Whitaker, S.; ";Progress in the development of a new high heat load X-ray tube";"Proceedings of the SPIE—The International Society for Optical Engineering 914 (A)"; Dec. 31, 1988; pp. 219-230.

* cited by examiner

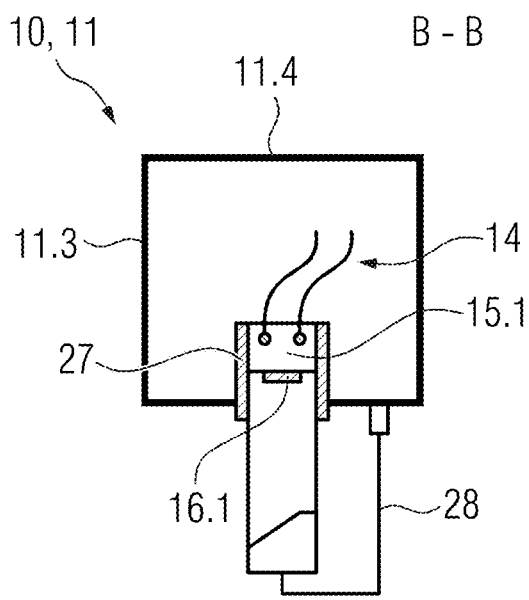
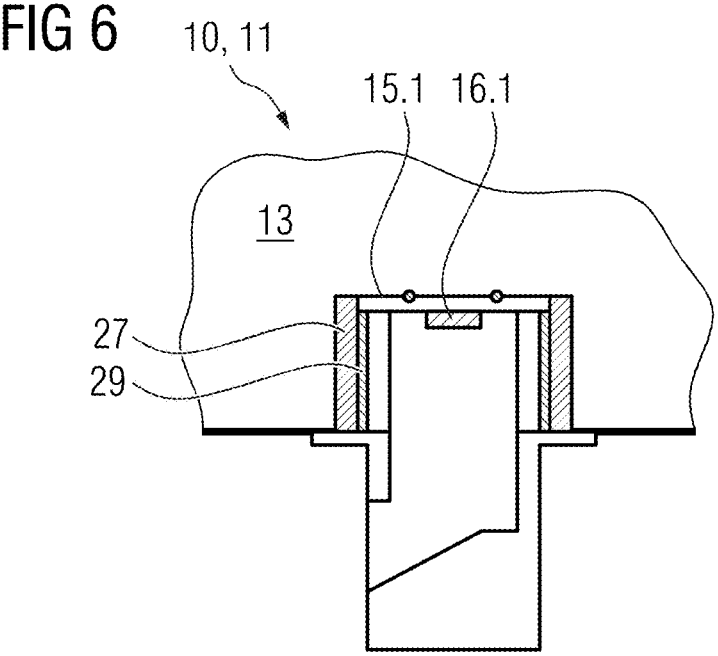

X-RAY EMITTER HOUSING WITH AT LEAST ONE ELECTRICALLY CONDUCTIVE HOUSING PORTION

CROSS-REFERENCE TO RELATED APPLICATION(S)

The present application claims priority under 35 U.S.C. § 119 to European Patent Application No. 22187531.3, filed Jul. 28, 2022, the entire contents of which are incorporated herein by reference.

FIELD

One or more example embodiments of the present invention relate to a multitube X-ray emitter housing, a multitube X-ray source, an X-ray facility or device and/or a computed tomography facility or device.

BACKGROUND

A typical X-ray tube of an X-ray source is only able to generate X-rays in a focal spot with an area in the millimeter or low centimeter range. Since some imaging system applications require fluoroscopy of a larger examination region via X-rays, as a rule, it is necessary to use sometimes complex mechanisms in order to move one single X-ray tube or even two individual X-ray tubes for fluoroscopy of the larger examination region.

Imaging systems with distributed X-ray sources are in particular characterized by the fact that the X-ray sources, in particular a large number thereof, are spatially distributed. With such an imaging system, there is in particular no need for mechanisms to move individual X-ray tubes. Fluoroscopy of the larger examination region can then in particular be performed by the spatially distributed X-ray sources without traversing mechanisms. In particular, in the case of an imaging system embodied as a computed tomography facility, it may be important for the focal spots on the anodes to have as small a spacing as possible and as constant spacing as possible. In particular, the small spacing is technically challenging due to the high voltage-conducting electrodes in the X-ray tube or the high voltage-conducting high-voltage contacts.

EP 3 586 752 A1 discloses a static imaging system with a multifocal annular X-ray source and an annular photon detector, wherein the X-ray source is composed of a plurality of X-ray tubes in an annular arrangement and wherein each X-ray tube generates a wide beam of X-rays directed toward the examination object. This imaging system is typified by the fact that the X-ray tubes must be mutually insulated from high-voltage and each X-ray tube must have its own individual high-voltage supply.

U.S. Pat. No. 11,183,357 B2 discloses a multibeam X-ray tube comprising an anode equipped as a cooling finger in an evacuated housing, wherein the housing has a plurality of cathode leads and no more than two high-voltage bushings and wherein a liquid cooling medium can flow in the high-voltage bushing. It is in particular typical of such an imaging system that all side surfaces of the evacuated housing are at ground potential and that an insulation distance has to be maintained between the anode or the cathode and the side surface. As a result, typically, the distance between a plurality of multibeam X-ray tubes is relatively large and the distance between focal spots on the anode can vary. A further disadvantage relates to the comparatively complex structure which, in particular in the case of one or more defective cathodes, may involve a complete replacement of the multibeam X-ray tube.

SUMMARY

One or more example embodiments of the present invention are based on the object of disclosing a multitube X-ray emitter housing, a multitube X-ray source, an X-ray facility (or device) and/or a computed tomography facility (or device) in which the X-ray tubes can be arranged in a more uniformly distributed manner and can be replaced more easily.

At least this object is achieved at least by the features of the independent claims. Advantageous embodiments are described in the subclaims and the disclosure.

The multitube X-ray emitter housing according to an embodiment of the present invention has
a housing with at least one side surface,
a high-voltage supply and
a cooling facility (or device) with an electrically insulating cooling medium,
wherein, inside the housing, the high-voltage supply has a single high-voltage supply lead for conducting a high voltage and a plurality of high-voltage contacts connected in parallel on the single high-voltage supply lead,
wherein the high-voltage contacts are in each case coupled to a high-voltage electrode to provide the high voltage and are at the same high-voltage potential,
wherein a first of the at least one side surface has a first electrically conductive housing portion with a temperature-dependent electrical conductivity,
wherein electrically insulating cooling medium is located between the first electrically conductive housing portion and one of the high-voltage contacts,
characterized
by a control unit, which has an interface for receiving a measured value representing the electrical conductivity of the first electrically conductive housing portion and is embodied to compare the measured value with a threshold value and by a switching facility (or device) for switching off the high voltage in dependence on the result of the comparison.

The first electrically conductive housing portion typically causes a current to flow through this housing portion on the application of high voltage. Advantageously, this results in a substantially linear potential profile along the first electrically conductive housing portion. In particular, scattered electrons can preferably be dissipated via the first electrically conductive housing portion and can hence reduce or prevent electrical charging. Accordingly, a further advantage relates to the reduction in creepage distances and/or shielding facilities for electrical charging in the first electrically conductive housing portion.

One advantage of the multitube X-ray emitter housing is that, compared to a conventional housing, at least one side surface does not have to consist of (highly) insulating components in order to insulate the high voltage between one of the high-voltage contacts and the housing. Preferably, the fact that the at least one side surface has a first electrically conductive housing portion enables conventional insulation measures, such as, for example, an appropriate insulation distance, to be at least partially mitigated or completely replaced.

The multitube X-ray emitter housing with the first electrically conductive housing portion advantageously enables the high-voltage contacts to be arranged closer overall to the housing and hence also to further high-voltage contacts of a further multitube X-ray emitter housing.

The multitube X-ray emitter housing can in principle be called a single-tank housing or monoblock housing. The multitube X-ray emitter housing is in particular a housing which is in principle suitable for at least partially accommodating a plurality of X-ray tubes and/or containing the high-voltage supply for the plurality of X-ray tubes As a rule, the multitube X-ray emitter housing does not have any X-ray-generating components, such as, for example, the plurality of X-ray tubes. In other words, it is not necessary for X-ray tubes or other X-ray-generating components to be coupled to the multitube X-ray emitter housing, but they may be coupled thereto. The multitube X-ray emitter housing can in particular couple a plurality of X-ray tubes in order to generate X-rays via the high voltage conducted and in particular cannot generate X-rays without the plurality of X-ray tubes.

The high-voltage supply is at least partially arranged inside the housing. The high-voltage supply in particular has a high-voltage generator, which can be arranged inside or outside the housing. The high-voltage generator in particular provides the high voltage at an output in dependence on a low voltage or mains voltage applied to an input. For this purpose, the high-voltage generator may include a transformer and/or a rectifier. If the high-voltage generator is arranged inside the housing, the low voltage or mains voltage can, for example, be fed from the outside into the housing at the input of the high-voltage generator via a plug integrated in the housing. Alternatively, the plug can be a high-voltage plug if the high-voltage generator is arranged outside the housing.

The high voltage is in particular DC voltage and/or is, for example, between 20 and 200 kV, in particular more than 40 kV and/or less than 150 kV. The high-voltage supply typically taps the high voltage provided at the output and conducts the tapped high voltage in the single high-voltage supply lead. The high voltage in particular serves to accelerate electrons inside an X-ray tube.

The single high-voltage supply lead in particular ensures that the plurality of high-voltage contacts conduct the same high voltage. This in particular reduces the complexity of the high-voltage supply because the high-voltage contacts connected in parallel are at the same high-voltage potential. The plurality of high-voltage contacts include at least two high-voltage contacts, in particular a first high-voltage contact and a second high-voltage contact. The single high-voltage supply lead can include a high-voltage cable and/or a circuit board. The single high-voltage supply lead can be embodied as electrically insulated, for example by appropriate shielding of the part conducting the high voltage.

The fact that the high-voltage contacts can in each case be coupled to a high-voltage electrode in particular means that an electrically conductive connection between a high-voltage contact and a high-voltage electrode only exists when they are coupled to one another. In other words, an electrically conductive connection is only formed when the coupling has taken place. The high voltage is typically applied to one of the high-voltage electrodes when that high-voltage electrode is coupled to the respective high-voltage contact. If a high-voltage electrode is not coupled to a high-voltage contact, the high voltage is in particular not applied to such a high-voltage electrode. As a rule, the high-voltage contacts are not completely electrically insulated in order to enable coupling. The high-voltage contacts are in particular contactable, for example by a high-voltage electrode.

The housing has at least one side surface. The housing in particular forms a container which can contain the high-voltage supply and/or the couplable X-ray tubes. The at least one side surface spatially surrounds, for example, the high-voltage supply and/or the electrically insulating cooling medium. The housing can typically have a plurality of side surfaces. Some of the side surfaces can be permanently connected to one another and/or embodied integrally. It is conceivable that one side surface is attached to another side surface via a hinge and, for example, forms a cover of the housing. Incidentally, in this case, the term side surface in particular explicitly includes an upper side and/or a lower side of the housing. In other words, 'side surface' means each side of the housing regardless of the orientation of the housing.

The at least one side surface can have a planar housing portion, a curved housing portion or a housing portion comprising a surface-enlarging structure. The surface-enlarging structure includes, for example, cooling ribs or cooling fins and can in particular act as a particularly suitable cooling apparatus with improved cooling properties with respect to a planar housing portion or a curved portion. It is conceivable that a side surface has a plurality of housing portions, which can be embodied as identical or different with respect to their material composition and/or surface finish. The side surface can in principle consist of or frame an electrically conductive housing portion. The frame, can, for example, be made of an electrically insulating material.

A second side surface of the housing can have a second electrically conductive housing portion. The second electrically conductive housing portion can be embodied such that this housing portion has the same electrical conductivity as the first electrically conductive housing portion. The first electrically conductive housing portion and the second electrically conductive housing portion are typically arranged on opposite sides of the housing. Other side surfaces of the housing can in particular be embodied as electrically insulating. As a rule, an X-ray exit window is integrated into a side surface of the housing.

The first electrically conductive housing portion has a temperature-dependent electrical conductivity, which is in particular dependent on the material or the material composition of the housing portion and, as a rule, on the temperature. In general, materials can differ in dependence on their respective electrical conductivity and be roughly classified as insulators (non-conductors), semi-conductors, conductors or superconductors. Transition between the classes is typically fluid. The material and/or the material composition of the first electrically conductive housing portion can in particular be insulating at a first temperature, "slightly" conductive at a higher temperature and "normally conductive" at a yet higher temperature.

The first electrically conductive housing portion is in particular embodied as not-perfectly insulating or weakly conductive at the operating temperature. The material or the material composition of the housing portion can be classified as insulator or non-conductor according to the definitions in https://de.wikipedia.org/wiki/Elektrische_Leitfähigkeit, but preferably in particular belongs to one of the classes 'semi-conductor', 'conductor' or 'superconductor'. Typically, the first electrically conductive housing portion can be embodied such that the electrical conductivity is at least $10^{-8}$ S/m at a lower temperature threshold value and/or at most $10^{-4}$ S/m at an upper temperature threshold value. According to Wikipedia, the first electrically conductive housing portion is not a so-called good insulator. A current flow along the first electrically conductive housing portion is in particular deliberately allowed and preferably desired from a minimum amplitude value and/or up to a maximum amplitude value. The amount of charge bled off via the first electrically conductive housing portion is in particular bled off to a ground point and/or to a protective conductor. The first electrically conductive housing portion typically acts as a capacitor and/or the amount of charge is discharged through the first electrically conductive housing portion or at its surface, for example in the direction of the cathode or a cathode part located at a short distance from this housing portion. The electric current, i.e., the amount of charge, flows, for example, through the electrically insulating cooling medium and/or to a second electrically conductive housing portion.

The lower temperature threshold value is, for example, at least −50 C °, preferably more than 0 C °. The maximum upper temperature threshold value is in particular 500 C °, preferably less than 100 C °. The operating temperature is in particular between the lower temperature threshold value and the upper temperature threshold value. The operating temperature can in particular correspond to a room temperature or a temperature window from 5° C. as the lower temperature threshold value to 25° C. as the upper temperature threshold value, preferably 20° to 25° according to the information in Wikipedia. The material or the material composition in particular has a breakdown voltage, which is higher than the high voltage.

The cooling facility (or device) has the electrically insulating cooling medium. The electrically insulating cooling medium is in particular not a vacuum. The electrically insulating cooling medium is in particular a fluid, in particular liquid and/or gaseous. The electrically insulating cooling medium is preferably arranged inside the housing, but can in principle alternatively or additionally flow around the housing. The housing can in particular be embodied as fluid-tight.

The fact that electrically insulating cooling medium is located between the first electrically conductive housing portion and one of the high-voltage contacts in particular means that the housing includes sufficient cooling medium for the cooling medium to cover at least the direct line of sight between the first electrically conductive housing portion and one of the high-voltage contacts. For this purpose, this high-voltage contact and the first electrically conductive housing portion can be positioned appropriately inside the housing. Advantageously, a distance between the first electrically conductive housing portion and one of the high-voltage contacts is less than an insulation distance along the electrically insulating cooling medium. In other words, an insulation capability of the cooling medium and/or the amount and/or volume of cooling medium between the first electrically conductive housing portion and one of the high-voltage contacts is too low to guarantee insulation and/or dielectric strength during operation of the multitube X-ray emitter housing. Insulation from high voltage is advantageously at least partially taken over by the linear potential profile along the first electrically conductive housing portion so that the operation of the multitube X-ray emitter housing is permissible according to the regulations.

The housing can in principle be completely filled with the cooling medium. In this case, the multitube X-ray emitter housing typically has an expansion compensation vessel and/or a pressure valve inside the housing.

The multitube X-ray emitter housing in particular has the control unit and the switching facility. The control unit can receive and in particular process the measured value. The processing includes, for example, comparing the measured value with the threshold value. The processing, in particular the comparison, of the measured value can take place according to program code. The control unit can have a computing module or logic module for executing the program code and/or a memory unit for storing and/or providing the threshold value. When comparing the measured value with the threshold value, in particular the result of the comparison is calculated or determined. The control unit can receive the measured value, which is usually time-resolved, in a clocked or repeated manner and/or compare it with the threshold value. The threshold value is usually constant. In principle, it is conceivable that the threshold value is not constant, but variable, in particular in dependence on operating times and/or operating parameters of the multitube X-ray emitter housing that are planned for the future.

The operation of the multitube X-ray emitter housing is typically dependent on compliance with regulatory standards and/or legal specifications and/or specifications of the manufacturer of the multitube X-ray emitter housing. Such standards and/or specifications in particular relate to safe operation of the X-ray emitter housing in order to minimize hazards for a user of the multitube X-ray emitter housing and/or to a patient. In this regard, in particular generally known standards are used to insulate high-voltage conducting components. Hence, this aspect in particular relates to the feature according to an embodiment of the present invention according to which the first housing portion is embodied as electrically conductive. As explained above, its conductivity depends inter alia on its temperature which may increase during operation in dependence on the operating parameters.

The result of the comparison in particular indicates the degree to which operation of the multitube X-ray emitter housing can be continued or whether switch-off should take place. It is conceivable that the result of the comparison indicates that switch-off is maintained. The result of the comparison can additionally typically indicate that the high voltage is switched on. In this case, the switching facility is embodied to switch on the high voltage in dependence on the result of the comparison. The result of the comparison is in particular binary and/or usually variable over time.

The switching facility can be connected to the high-voltage supply to switch off and/or to switch on the high voltage. Alternatively or additionally, the switching facility can include one or more switches which interrupt the conduction of the high voltage in the single high-voltage supply lead after switch-off of the high voltage and/or enable the high voltage to be conducted in the single high-voltage supply lead after switch-off of the high voltage. A further alternative relates to the possibility that the high-voltage generator is switched off during switch-off or switched on during switch-on.

One embodiment provides that the cooling facility has a cooling apparatus embodied to stabilize the temperature of the first electrically conductive housing portion above a lower temperature threshold value and/or below an upper temperature threshold value. The temperature stabilization of the first electrically conductive housing portion in particular controls the temperature-dependent electrical conductivity. Controlling the temperature-dependent electrical conductivity in particular includes stabilizing and/or limiting and/or establishing the current dropping across the first electrically conductive housing portion. The temperature stabilization of the first electrically conductive housing portion advantageously enables the substantially linear potential profile along the first electrically conductive housing portion to be maintained during operation of the multitube X-ray emitter housing. The cooling apparatus can be embodied as active or passive. An example of the passive embodiment is, for example, one with an appropriate dimensioning or shape of the surface of the housing, in particular a side surface. The shape of the surface can include the surface-enlarging structure. An example of the active embodiment is one with which the cooling apparatus has a fluid-cooling medium heat exchanger and/or can effect forced convection. In this case, the temperature stabilization of the cooling medium in particular includes setting, preferably increasing and/or reducing, the temperature of the cooling medium. The active cooling apparatus in particular sets the temperature of the cooling medium such that the temperature at the first electrically conductive housing portion is above the lower temperature threshold value and/or below the upper temperature threshold value. The lower temperature threshold value and the upper temperature threshold value in particular form a temperature interval in which the operating temperature of the first electrically conductive housing portion preferably lies. The upper temperature threshold value and/or the lower temperature threshold value can in particular be stored in the memory unit. The cooling apparatus can preferably access the stored upper temperature threshold value and/or lower temperature threshold value via an interface.

One embodiment provides that the cooling apparatus is embodied to stabilize the temperature of the cooling medium which is located inside and/or outside the housing and interacts directly with the first electrically conductive housing portion. This embodiment is in particular advantageous because herein the temperature stabilization takes place closer to or directly at the first electrically conductive housing portion and hence preferably takes place more quickly and/or more precisely.

One embodiment provides that the multitube X-ray emitter housing furthermore has a temperature sensor for measuring a temperature value representing the electrical conductivity of the first electrically conductive housing portion as a measured value. In particular the cooling apparatus is embodied to stabilize the temperature of the cooling medium in dependence on the temperature value. This embodiment in particular enables direct control of the temperature of the cooling medium.

One embodiment provides that the multitube X-ray emitter housing furthermore has a current sensor for measuring a current value flowing away via the first conductive housing portion as a measured value. The measurement can in particular take place by measuring a current between the cathode and the anode and/or a current between the anode to ground and/or a current between the cathode to ground, which, as a rule, represent the sum over all current paths. Preferably, the current value can be derived or determined therefrom. In particular the cooling apparatus is embodied to stabilize the temperature of the cooling medium in dependence on the current value. The current value in particular represents the current flowing away via the first conductive housing portion. In this embodiment, the upper temperature threshold value and/or the lower temperature threshold value can be assigned to or substantially correspond to an upper current threshold value or a lower current threshold value. The threshold values can have been assigned in an assignment table, which is, for example, stored in the memory unit.

One embodiment provides that the first electrically conductive housing portion has flint glass, proceram, silicon nitride, silicon carbide, zirconia, silicon and/or a doped material. It is in principle conceivable that the first electrically conductive housing portion has exclusively one of the aforementioned electrically conductive materials or a combination of the aforementioned electrically conductive materials in a material composition. The material composition can include different layers with one or more of the aforementioned electrically conductive materials. It is conceivable that one of the layers is embodied as a carrier layer and/or another layer is embodied as a coating. In particular, the coating can include one of the aforementioned electrically conductive materials. The material composition can in principle include further materials, typically insulating materials such as glass, plastic, etc., which are, for example, used as a carrier layer. As an alternative to the layer structure, the material composition can be present in a mixed form, for example consisting of a solidified powder.

One embodiment provides that the multitube X-ray emitter housing has a first bushing for accommodating a first high-voltage contact, wherein the first bushing has an attaching device (or, alternatively, mechanism or means), in particular a clamping device (or, alternatively, mechanism or means), a screwing device (or, alternatively, mechanism or means) and/or a plug-in device (or, alternatively, mechanism or means) for detachably coupling a first high-voltage electrode to the first high-voltage contact. This embodiment advantageously enables easy replacement of the first high-voltage electrode or the component containing the first high-voltage electrode, for example an X-ray tube. The detachable coupling in particular includes coupling and/or decoupling. In principle, it is conceivable that additionally a second bushing or further bushings, which can be embodied in a substantially identical design, are arranged in the housing. Furthermore, it is conceivable that, for each high-voltage contact, in each case a high-voltage electrode can be detachably coupled in each individual bushing.

One embodiment provides that an insulating grommet for electrically insulating the couplable high-voltage electrode from the first bushing is arranged in the first bushing. In this embodiment, in particular the electrical contact between the first high-voltage electrode with the first high-voltage contact is improved. In principle, all bushings can be structured in this way.

One embodiment provides that the first bushing is made of a material with a temperature-dependent electrical conductivity. In this embodiment, in particular the high-voltage insulation between the first high-voltage electrode and the first high-voltage contact can be simplified because, advantageously, a linear potential profile is established along the first bushing and this shares the advantages described in connection with the first electrically conductive housing portion.

The first bushing can hence be constructed from the same material and/or the same material composition as the first electrically conductive housing portion. In principle, all bushings can be constructed in this way.

One embodiment provides that a sealing facility (or seal, seal mechanism or seal device) for sealing the housing is arranged between the first bushing and the housing. In this embodiment, the bushing is in particular part of the housing and integrated into a side surface of the housing. It is in principle conceivable that the bushing is integrated into the first of the at least one side surface with the first electrically conductive housing portion. 'Integrated' in particular means that the housing has a recess that enables the first bushing to be attached to the housing and the first bushing to penetrate the housing. The sealing in particular prevents leakage of the cooling medium through the technically necessary gap between the first bushing and the housing. In principle, an individual sealing facility for sealing the housing can be arranged for each such bushing.

A multitube X-ray source according to an embodiment of the present invention has
 at least one multitube X-ray emitter housing and
 a plurality of X-ray tubes,
wherein each X-ray tube includes a vacuum housing with a cathode and an anode for generating X-rays, wherein an acceleration path for emitted electrons is provided between the cathode and the anode and
wherein the anodes or the cathodes form the high-voltage electrodes and are in each case coupled to the high-voltage contacts.

The multitube X-ray source according to an embodiment of the present invention has the at least one multitube X-ray emitter housing and hence shares the above-described advantages and embodiment thereof.

The multitube X-ray source can advantageously be composed of a plurality of multitube X-ray emitter housings into which the X-ray tubes are inserted. The distance between the respective multitube X-ray emitter housings can advantageously be minimized or equal to zero because the first electrically conductive housing portion enables insulation from the high voltage inside the respective multitube X-ray emitter housings, in particular when at least one individual housing portion of one of the multitube X-ray emitter housings of this kind is arranged spatially between adjacent multitube X-ray emitter housings. Advantageously, the respective electrically conductive housing portions are arranged one next to the other. Hence, the multitube X-ray source according to an embodiment of the present invention can advantageously be constructed such that the distance between at least two X-ray tubes that are in each case inserted in different adjacent multitube X-ray emitter housings is the same as the distance between adjacent X-ray tubes inside one multitube X-ray emitter housing. In other words, the distance between adjacent X-ray tubes and hence typically the focal spot on the anode is equidistant regardless of whether the adjacent X-ray tubes are inserted in the same or different multitube X-ray emitter housings.

The vacuum housing of one of the X-ray tubes can be at least partially surrounded by the electrically insulating cooling medium. Electrically insulating cooling medium can be located between a portion of the vacuum housing and the first electrically conductive housing portion. The first electrically conductive housing portion is preferably arranged substantially parallel to the closest acceleration path or the acceleration paths. In other words, the X-ray tubes closest to the first electrically conductive housing portion are typically oriented parallel or substantially parallel or at an acute angle to this housing portion. In this case, the first electrically conductive housing portion preferably has an extension parallel to the acceleration path corresponding at least to the length of the closest acceleration path.

The plurality of X-ray tubes can in principle be oriented in parallel or in a fan shape. This orientation in particular relates to the central beam of the X-rays generated in each case. In other words, the vacuum housings can in principle be aligned substantially parallel with the acceleration paths of the plurality of X-ray tubes and, at the same time, when the X-rays are emitted perpendicular to the acceleration paths, the X-rays can be oriented in a fan shape by the rotation of individual X-ray tubes.

Typically, each X-ray tube, considered alone, is embodied for the imaging examination of a patient. Alternatively, an X-ray tube can be provided for a material examination. The imaging examination can in particular be angiography, computed tomography, mammography or radiography.

The emitted X-rays are typically directed at an examination region, for example with the patient or the material. X-rays from a single X-ray tube usually cover a part of the examination region, which may be up to and including 100%. Alternatively, the single X-ray tube may not cover 100%, in particular may cover less than 100% of the examination region. Preferably, the X-rays from all or at least part of the X-ray tubes cover 100% of the examination region i.e., all of it.

The plurality of X-ray tubes can typically be actuated such that they can emit X-rays simultaneously or consecutively. An X-ray emission sequence may include two adjacent X-ray tubes emitting X-rays simultaneously during a transition time that is shorter than the time of the X-ray emission per X-ray tube. Actuation methods for the plurality of X-ray tubes in particular enable an imaging examination, for example comprising two-dimensional fluoroscopy, tomosynthesis or projection-based three-dimensional volume reconstruction.

The plurality of X-ray tubes are advantageously of identical construction. The higher quantities mean there can typically be a price advantage. Additionally, the identical construction enables fewer different components to be installed in the multitube X-ray emitter housing, which can inter alia simplify maintenance. Alternatively, in principle, one X-ray tube can differ from another X-ray tube, in particular with respect to the embodiment of the anode and/or cathode.

The following describes a possible embodiment of an X-ray tube, which can in principle apply to the other X-ray tubes:

The cathode typically includes an electron emitter. The electron emitter is embodied to generate a focal spot on the anode via electrons. The electron emitter can have a field-effect emitter or a thermionic emitter. The thermionic emitter can be a helical emitter or flat emitter.

With a field-effect emitter, electron emission is typically effected by the application of a gate voltage, which extracts electrons from nanotubes by the electric field occurring in the tips of these nanotubes as a result of which the electron current is formed. In addition to switching via the gate voltage, a generated electron current can be blocked via a blocking grid. The field-effect emitter typically has a plurality of nanotubes made, for example, of carbon or silicon or molybdenum.

The emitted electrons are accelerated by the electron emitter in the direction of the anode along the acceleration path and generate the X-rays upon interaction in the focal spot. The X-rays generated usually have a maximum energy of up to 150 keV in dependence on the accelerating voltage applied between the electron emitter and the anode. With a unipolar X-ray tube, the accelerating voltage typically corresponds to the high voltage and, with a bipolar X-ray tube, is, as a rule, twice the amount of the high voltage.

The anode can be embodied as a rotating anode or standing anode. Standing anodes may be preferable for the present invention—these which typically have smaller housings and a less expensive design. A possibly lower X-ray dose with a standing anode compared to a rotary anode can, for example, be compensated by increasing the number of anodes.

One embodiment provides that the plurality of X-ray tubes are arranged completely inside the housing. In this case, the housing typically has the X-ray exit window, which is typically arranged close to the anode of the respective X-ray tubes. The X-ray exit window can be divided into a plurality of partial windows.

An alternative embodiment to the previous embodiment provides that at least one of the X-ray tubes protrudes from the housing such that X-rays generated at the anode propagate away from the housing. The fact that the generated X-rays propagate away from the housing in particular means that the X-rays can be generated outside the housing without attenuation at a side surface of the housing. The X-rays, or at least the central beam thereof, can in particular be oriented parallel or perpendicular or at an angle of between 0 and 90° to the housing surface. Particularly advantageously, all X-ray tubes protrude from the housing such that X-rays generated at the anodes propagate away from the housing.

In this embodiment, an X-ray tube can advantageously be replaced comparatively easily, in particular if the multitube X-ray emitter housing has the first bushing for accommodating the first high-voltage contact, wherein the first bushing has the clamping device, the screwing device and/or the plug-in device for detachably coupling the first high-voltage electrode to the first high-voltage contact. In this case, the coupled X-ray tube can be detached, for example for maintenance and/or replacement.

One embodiment provides that a distance between the first electrically conductive housing portion and one of the X-ray tubes is less than an intermediate insulation distance along electrically insulating cooling medium. This embodiment is in particular enabled by the fact that the linear potential profile is established due to the first electrically conductive housing portion and hence safe operation of the X-ray tube in question is ensured.

An X-ray facility (or device) according to according to an embodiment of the present invention has the multitube X-ray source and
an X-ray detector.

The X-ray facility according to according to an embodiment of the present invention has the at least one multitube X-ray emitter housing and hence shares the above-described advantages and embodiment thereof.

The X-ray detector is embodied to detect the X-rays that propagate through the examination region. During detection, in particular an attenuation profile is acquired. The detected X-rays can be used in a reconstruction computer, for example according to the imaging examination, in order to reconstruct a 2D or 3D image. In principle, several series of images can also be reconstructed over time.

A computed tomography facility (or device) according to according to an embodiment of the present invention, having—a plurality of X-ray facilities, wherein the housings of the multitube X-ray emitter housings are embodied as arc-shaped, wherein the arc-shaped housings cover at least 180° and wherein a distance between adjacent X-ray tubes is equidistant.

The computed tomography facility according to according to an embodiment of the present invention has the at least one multitube X-ray emitter housing and hence shares the above-described advantages and embodiment thereof.

In other words, the plurality of X-ray facilities are in particular connected to one another or in contact with one another via the first electrically conductive housing portion. In an arc-shaped embodiment, a surface normal of the first electrically conductive housing portion is oriented substantially tangentially. Advantageously, the plurality of X-ray tubes, in particular the X-rays thereof, are oriented in a fan shape.

Features, advantages or alternative embodiments mentioned in the description of the apparatus can also be transferred to a method and vice versa. In other words, claims relating to the method can be developed with features of the apparatus. In particular, the apparatus according to according to one or more embodiments of the present invention can be used in the method.

BRIEF DESCRIPTION OF THE DRAWINGS

In the following, the present invention is described and explained in more detail with reference to the exemplary embodiments depicted in the figures. In principle, in the following description of the figures, structures and units that remain substantially the same are designated with the same reference symbol as that used on the first occurrence of the respective structure or unit.

The figures show.

DETAILED DESCRIPTION

Figure 1:
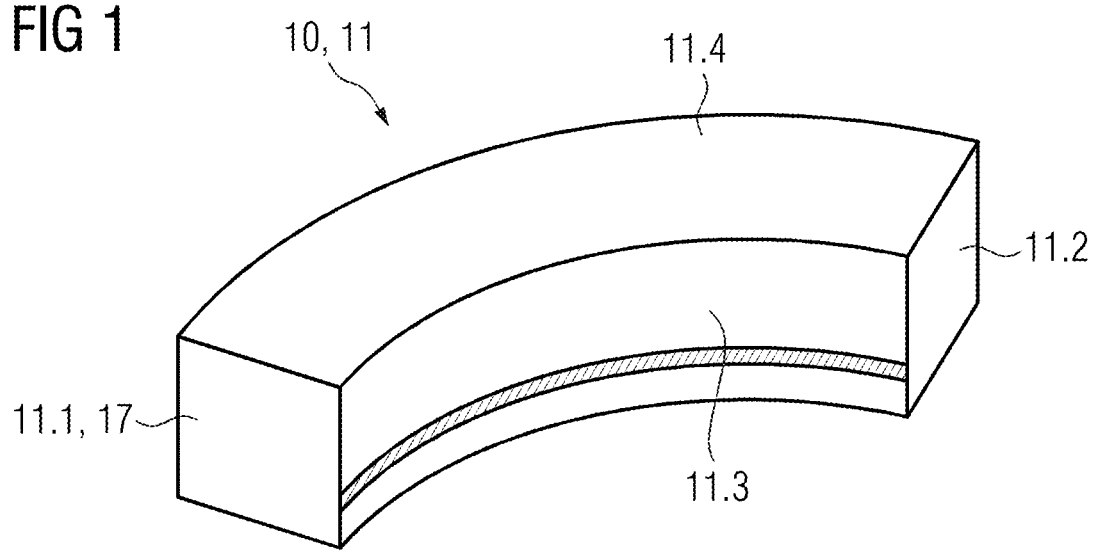
FIG. 1 a multitube X-ray emitter housing,
FIG. 2 a first exemplary embodiment of the multitube X-ray emitter housing,
FIG. 3 a second exemplary embodiment of the multitube X-ray emitter housing,
FIG. 4 a third exemplary embodiment of the multitube X-ray emitter housing,
FIG. 5 and FIG. 6 a fourth exemplary embodiment of the multitube X-ray emitter housing,
FIG. 7 a multitube X-ray source,
FIG. 8 a further exemplary embodiment of the multitube X-ray source, and
FIG. 9 an X-ray facility.

FIG. 1 shows a perspective view of a multitube X-ray emitter housing 10.

The multitube X-ray emitter housing 10 has a housing 11 with at least one side surface 11.1 . . . 11.N. Inside the housing 11, the multitube X-ray emitter housing 10 has a high-voltage supply 12 and a cooling facility with an electrically insulating cooling medium 13, which, in FIG. 1, are covered by the side surfaces 11.1 . . . 11.N.

In FIG. 1, the housing 11 is embodied as curved in an arc shape as an elongated rod. A surface normal of the first electrically conductive housing portion 17 is hence oriented substantially tangentially. Alternatively, the housing 11 can be embodied as non-curved, in particular straight.

Inside the housing 11, the high-voltage supply 12 has a single high-voltage supply lead 14 for conducting a high voltage and a plurality of high-voltage contacts 15.1 . . . 15.N connected in parallel on the single high-voltage supply lead 14. The high-voltage contacts 15.1 . . . 15.N can in each case be coupled to a high-voltage electrode 16.1 . . . 16.N to provide the high voltage and are at the same high-voltage potential.

A first of the at least one side surfaces 11.1 . . . 11.N has a first electrically conductive housing portion 17 with a temperature-dependent electrical conductivity. In the exemplary embodiment shown in FIG. 1, the side surface designated 11.1 is embodied in such a way. A further preferred side surface is the side surface designated 11.2. For example, this or both side surfaces 11.1, 11.2 could have a first 17 or second electrically conductive housing portion. Obviously, the other side surfaces 11.3, 11.4 or the averted side surfaces 11.N could also have an electrically conductive housing portion. Electrically insulating cooling medium 13 is located between the first electrically conductive housing portion 17 and one of the high-voltage contacts 15.1 . . . 15.N. The electrical conductivity is preferably at least $10^{-8}$ S/m at a lower temperature threshold value and/or at the most $10^{-4}$ S/m at an upper temperature threshold value. The first electrically conductive housing portion 17 in particular has flint glass, proceram, silicon nitride, silicon carbide, zirconia, silicon and/or a doped material.

The multitube X-ray emitter housing 10 furthermore has a control unit 18 and a switching facility 20 (not shown in FIG. 1). The control unit 18 has an interface 19 for receiving a measured value representing the electrical conductivity of the first electrically conductive housing portion 17 and is embodied to compare the measured value with a threshold value. The switching facility 20 is embodied to switch off the high voltage in dependence on the result of the comparison.

In FIG. 1, an optional X-ray exit window 21 is indicated in the side surface 11.3—depending on the embodiment, this can be provided in this side surface or in another side surface of the multitube X-ray emitter housing 10.

Figure 2:
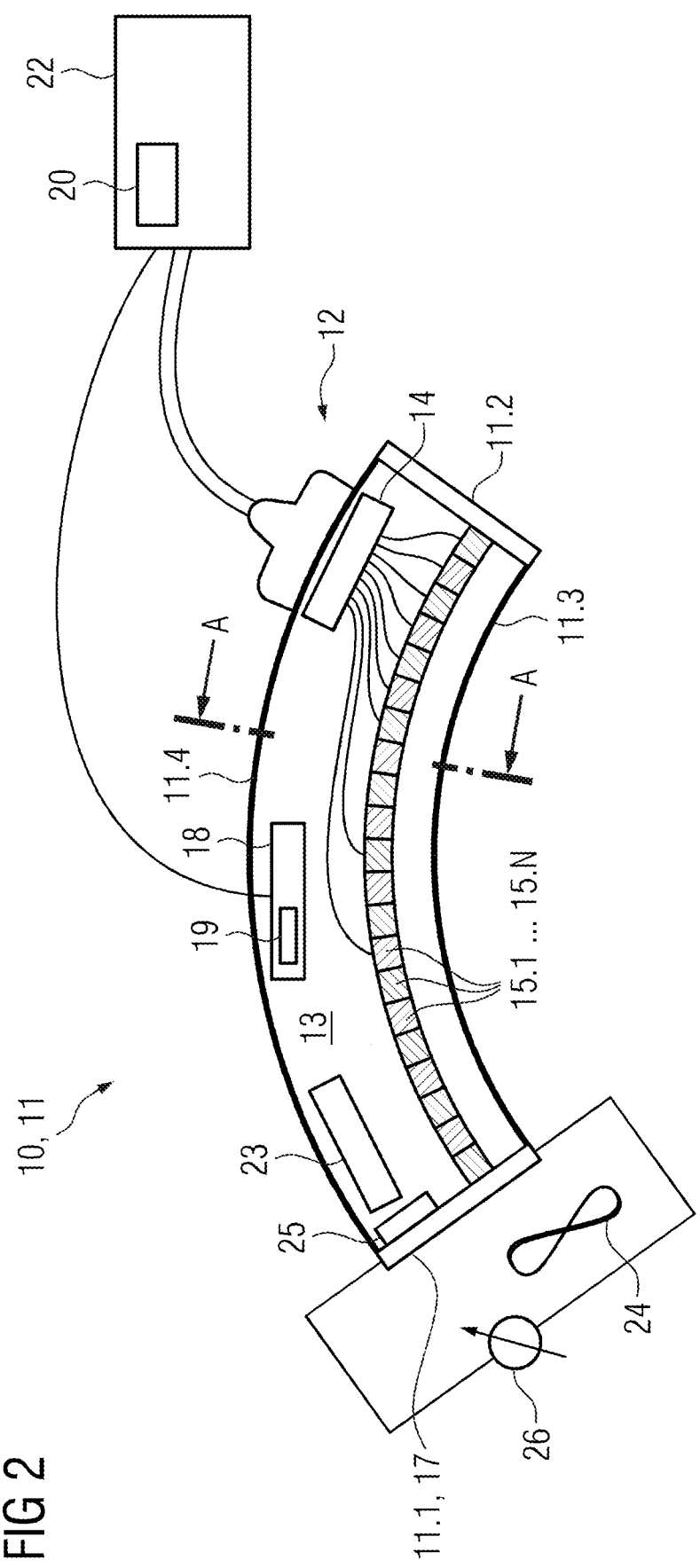

FIG. 2 shows a first exemplary embodiment of the multitube X-ray emitter housing 10 in cross section along the Advantageously, the cooling facility has a cooling apparatus 24, which is embodied to stabilize the temperature of the first electrically conductive housing portion 17 above a lower temperature threshold value and/or below an upper temperature threshold value. In this exemplary embodiment, the cooling apparatus 24 is embodied as active by way of example. The cooling apparatus 24 shown actively cools the first electrically conductive housing portion 17 via forced convection of the ambient air outside the housing 11. Hence, the cooling apparatus 24 is embodied to stabilize the temperature of the cooling medium which is located outside the housing 11 and interacts directly with the first electrically conductive housing portion 17. In an alternative embodiment (not shown), the cooling apparatus 24 can cool the cooling medium 13 located inside the housing 11.

In FIG. 2, the housing 11 is embodied as arc-shaped. In the arc-shaped embodiment, a surface normal of the first electrically conductive housing portion 17 is oriented substantially tangentially with respect to a center point of the arc.

The high-voltage supply 12 has a high-voltage generator 22 arranged outside the housing 11. The high-voltage generator 22 is connected to the high-voltage supply lead 14 via a cable. The high-voltage generator 22 comprises a switching facility 20 for switching off the high voltage. The control unit 18 is connected to the switching facility 20 for transmitting the result of the comparison or a switch-off signal. In this exemplary embodiment, the connection is wired, but it may alternatively be wireless.

The housing 11 comprises a plurality of high-voltage contacts 15.1 . . . 15.N. The number shown in FIG. 2 is for illustrative purposes only. The number is at least 2. The high-voltage supply lead 14 transmits the high voltage to the high-voltage contacts 15.1 . . . 15.N via galvanic connections, for example by cable or via conductor tracks connected in parallel. For reasons of clarity, only some of these connections are depicted in FIG. 2.

The side surface 11.1 has the first electrically conductive housing portion 17. The housing 11 comprises an expansion compensation vessel 23. Furthermore, the housing 11 includes the control unit 18, which can alternatively also be arranged outside the housing 11. The control unit 18 comprises the interface 19.

The multitube X-ray emitter housing 10 furthermore has a temperature sensor 25 for measuring a temperature value representing the electrical conductivity of the first electrically conductive housing portion 17 as a measured value and a current sensor 26 for measuring a current value flowing away via the first electrically conductive housing portion 17 as a measured value. The temperature sensor 25 is arranged inside the housing close to the first electrically conductive housing portion 17. In principle, it is possible to provide the temperature sensor 25 and/or the current sensor 26.

Figure 3:
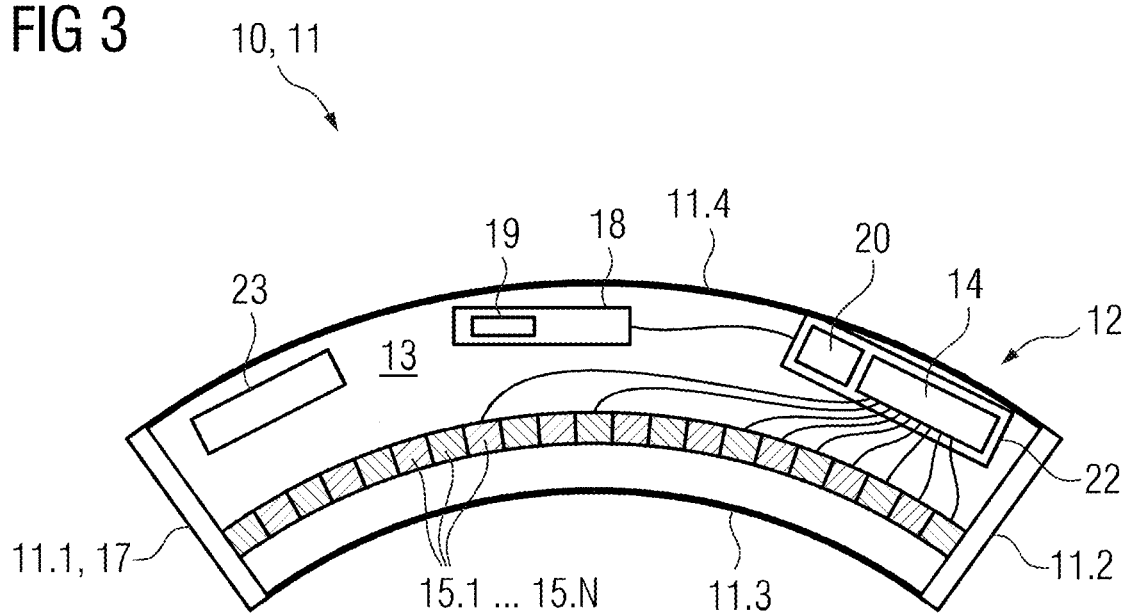

FIG. 3 shows a second exemplary embodiment of the multitube X-ray emitter housing 10 in cross section along the Compared to the exemplary embodiment shown in FIG. 2, the high-voltage generator 22 is arranged inside the housing 11. The cooling medium 13 can in particular be used to cool the high-voltage generator 22.

Figure 4:
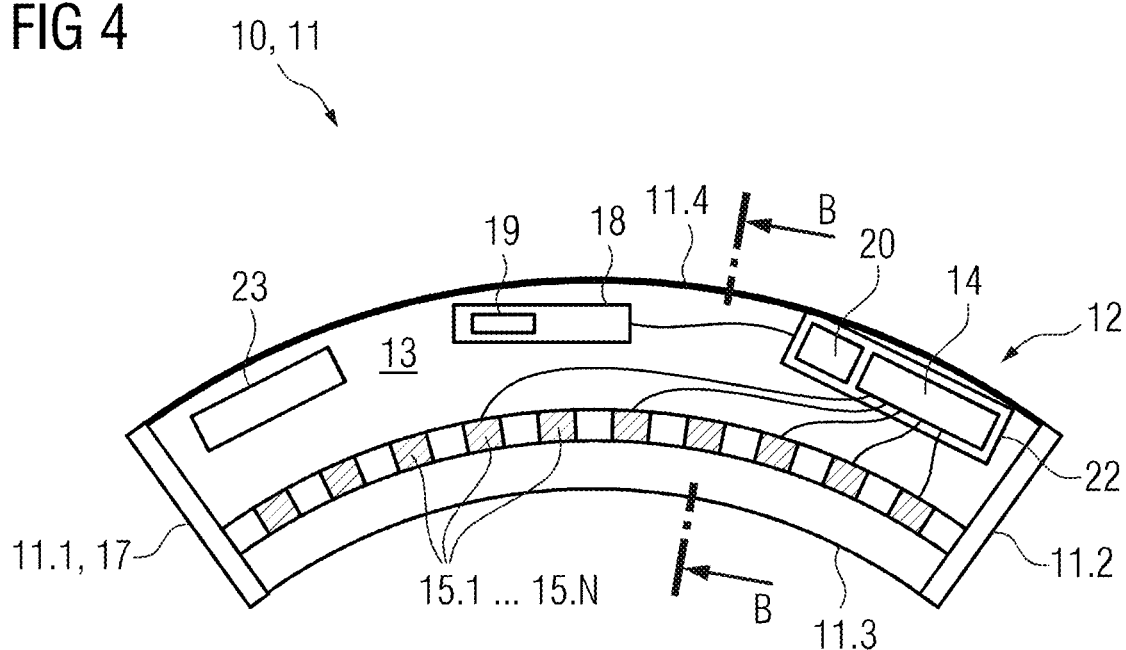

FIG. 4 shows a third exemplary embodiment of the multitube X-ray emitter housing 10 in cross section along the longitudinal axis.

The exemplary embodiment shown in FIG. 4 substantially corresponds to the exemplary embodiment in FIG. 3. The main difference is the distance between the high-voltage contacts 15.1 . . . 15.N in order to improve the ease of coupling and decoupling of X-ray tubes (not shown).

FIG. 5 shows a fourth exemplary embodiment of the multitube X-ray emitter housing 10 in cross section perpendicular to the longitudinal axis along B-B, as depicted in FIG. 4.

The multitube X-ray emitter housing 10 has a first bushing 27 for accommodating a first high-voltage contact 15.1. The first bushing 27 is a recess in the housing 11. The housing 11 has a U-shaped cross section, wherein the first bushing 27 is framed by the two legs. The first high-voltage contact 15.1 is arranged on the base of the first bushing 27.

The first bushing 27 has an attaching device (or, alternatively, mechanism or means) 28, in particular a clamping device (or, alternatively, mechanism or means), a screwing device (or, alternatively, mechanism or means) and/or a plug-in device (or, alternatively, mechanism or means), for detachably coupling a first high-voltage electrode 16.1 to the first high-voltage contact 15.1. FIG. 5 depicts an X-ray tube, which typically has a cathode and an anode. In this exemplary embodiment, the cathode forms the high-voltage electrode 16.1. The distance between the first high-voltage contact 15.1 and the first high-voltage electrode 16.1 is shown for illustrative purposes only. The attaching device 28 is embodied as a clamping device, in particular as a tension spring.

FIG. 6 shows the fourth exemplary embodiment of the multitube X-ray emitter housing 10 in an enlarged view.

An insulating grommet 29 for electrically insulating the couplable high-voltage electrode 15.1 from the first bushing 27 is arranged in the first bushing 27. The first bushing 27 is made of a material with a temperature-dependent electrical conductivity. The high-voltage electrode of the X-ray tube, i.e., the anode, which is not at high voltage, is preferably at ground potential.

Figure 7:
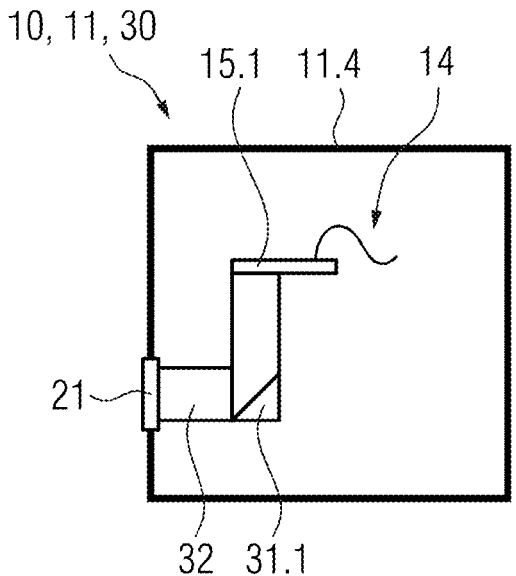

FIG. 7 shows a multitube X-ray source 30 in a cross section perpendicular to the longitudinal axis.

The multitube X-ray source 30 has at least one multitube X-ray emitter housing 10 and a plurality of X-ray tubes 31.1 . . . 31.N. Each X-ray tube 31.1 . . . 31.N comprises a vacuum housing with a cathode and an anode for generating X-rays. An acceleration path for emitted electrons is provided between the cathode and the anode. The cathodes, alternatively (but not shown) the anodes, form the high-voltage electrodes 16.1 . . . 16.N and are in each case coupled to the high-voltage contacts 15.1 . . . 15.N. FIG. 7 shows by way of example an X-ray tube 31.1 in a cross section perpendicular to the longitudinal axis. The other X-ray tubes can be embodied in the same way.

In the exemplary embodiment in FIG. 7, the X-ray tube 31.1 is arranged inside the housing 11. A collimator 32 is arranged between the anode and the X-ray exit window 21. The emitted X-rays leave the housing 11 through the X-ray exit window 21.

Figure 8:
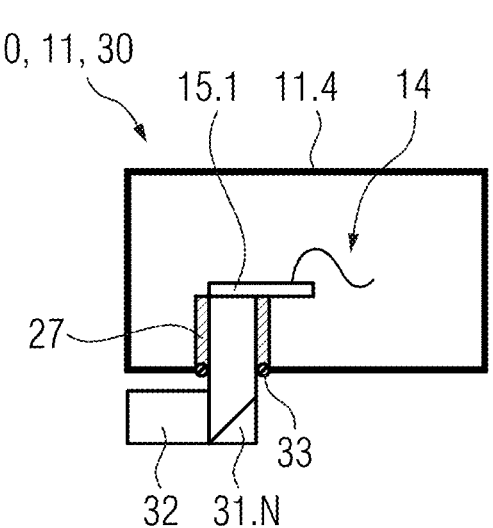

FIG. 8 shows a further exemplary embodiment of the multitube X-ray source 30.

At least one 31.N of the X-ray tubes protrudes from the housing 11 such that X-rays generated at the anode propagate away from the housing 11. In other words, the anode of the X-ray tube 31.N is located outside the housing 11. In principle, all X-ray tubes 31.1 . . . 31.N can be arranged outside the housing.

The multitube X-ray emitter housing 10 has the first bushing 27 for accommodating a high-voltage contact 15.N for detachably coupling the X-ray tube 31.N. A sealing facility 33 for sealing the housing 11 is arranged between the first bushing 27 and the housing 11. The sealing facility 33 can in particular be annular or polygonal in shape.

Figure 9:
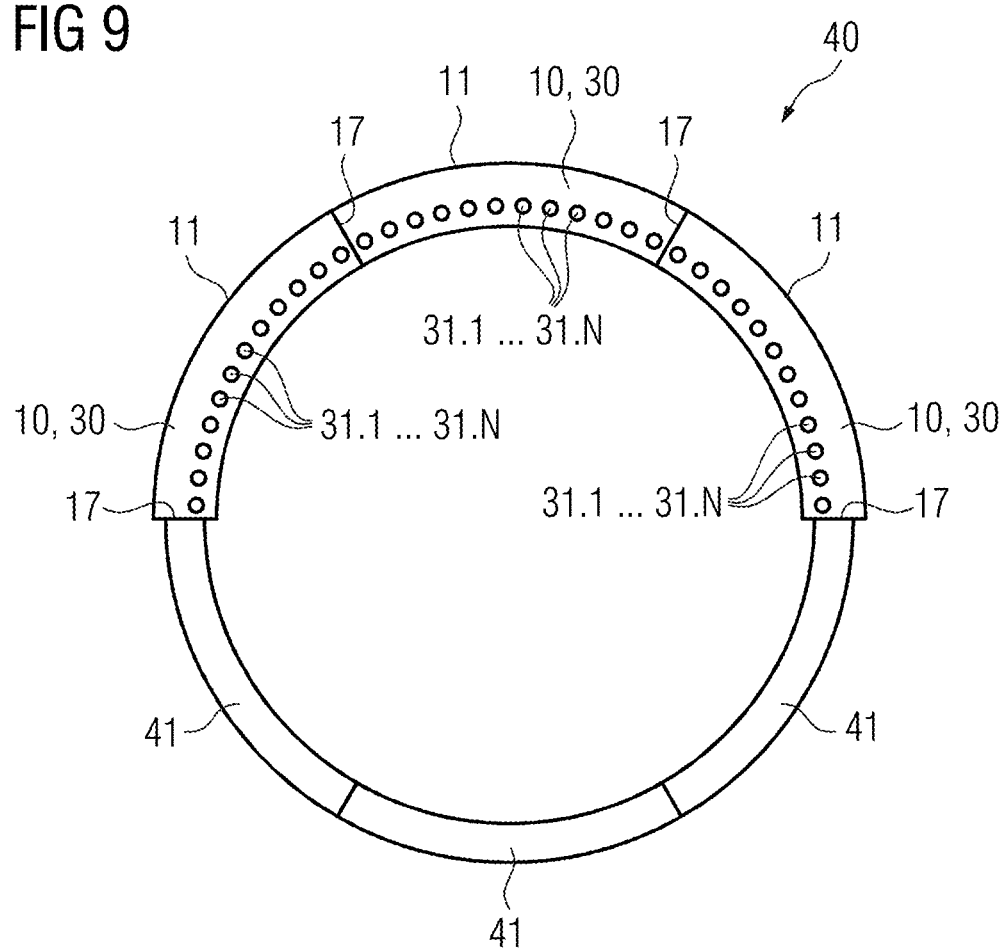

FIG. 9 shows a frontal view of an X-ray facility 40.

The X-ray facility 40 has the multitube X-ray source 30 and an X-ray detector 41. FIG. 9 shows a computed tomography facility having a plurality of X-ray facilities 40. The housings 11 of the multitube X-ray emitter housings 10 are embodied as arc-shaped. The arc-shaped housings 11 cover at least 180°. In principle, it is conceivable that a sufficient number of X-ray facilities 40 and/or longer arc-like housings 11 are used for the arc-shaped housings 11 to cover 360°.

In FIG. 9, the X-ray detector 41 covers 180° and is in each case arranged opposite the plurality of X-ray tubes 31.1 . . . 31.N. The X-ray detector 41 can consist of a plurality of individual detectors or form a continuous X-ray detector.

A distance between the adjacent X-ray tubes 31.1 . . . 31.N is equidistant. A distance between the first electrically conductive housing portion 17 and one of the X-ray tubes 31.1 . . . 31.N is lower than an intermediate insulation distance along electrically insulating cooling medium 13.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A multitube X-ray emitter housing, comprising:
a housing with at least one side surface;
a high-voltage supply;
a cooling device with an electrically insulating cooling medium, wherein
   inside the housing, the high-voltage supply has a single high-voltage supply lead to conduct a high voltage, and a plurality of high-voltage contacts connected in parallel on the single high-voltage supply lead,
   the plurality of high-voltage contacts, in each case, are configured to be coupled to a high-voltage electrode to provide the high voltage and are at a same high-voltage potential,
   a first of the at least one side surface has a first electrically conductive housing portion with a temperature-dependent electrical conductivity, and
   the electrically insulating cooling medium is located between the first electrically conductive housing portion and one of the plurality of high-voltage contacts;
a control unit having an interface configured to receive a measured value representing an electrical conductivity of the first electrically conductive housing portion, and to compare the measured value with a threshold value; and
a switching device configured to switch off the high voltage based on the comparison.

2. The multitube X-ray emitter housing as claimed in claim 1, wherein the cooling device has a cooling apparatus configured to stabilize a temperature of the first electrically conductive housing portion at least one of above a lower temperature threshold value or below an upper temperature threshold value.

3. The multitube X-ray emitter housing as claimed in claim 2, wherein the cooling apparatus is configured to stabilize a temperature of the electrically insulating cooling medium, which is located at least one of inside or outside the housing and interacts directly with the first electrically conductive housing portion.

4. The multitube X-ray emitter housing as claimed in claim 3, further including at least one of
a temperature sensor configured to measure a temperature value representing the electrical conductivity of the first electrically conductive housing portion as a measured value, or
a current sensor configured to measure a current value flowing away via the first electrically conductive housing portion as a measured value.

5. The multitube X-ray emitter housing as claimed in claim 3, further comprising:
a first bushing configured to accommodate a first high-voltage contact, wherein
   the first bushing includes an attaching device configured to detachably couple a first high-voltage electrode to the first high-voltage contact, and
   the attaching device includes at least one of a clamping device, a screwing device or a plug-in device.

6. The multitube X-ray emitter housing as claimed in claim 2, further comprising:
a first bushing configured to accommodate a first high-voltage contact, wherein
   the first bushing includes an attaching device configured to detachably couple a first high-voltage electrode to the first high-voltage contact, and
   the attaching device includes at least one of a clamping device, a screwing device or a plug-in device.

7. The multitube X-ray emitter housing as claimed in claim 1, further including at least one of
 a temperature sensor configured to measure a temperature value representing the electrical conductivity of the first electrically conductive housing portion as a measured value, or
 a current sensor configured to measure a current value flowing away via the first electrically conductive housing portion as a measured value.

8. The multitube X-ray emitter housing as claimed in claim 7, further comprising:
 a first bushing configured to accommodate a first high-voltage contact, wherein
  the first bushing includes an attaching device configured to detachably couple a first high-voltage electrode to the first high-voltage contact, and
  the attaching device includes at least one of a clamping device, a screwing device or a plug-in device.

9. The multitube X-ray emitter housing as claimed in claim 1, wherein the electrical conductivity is at least one of at least $10^{-8}$ S/m at a lower temperature threshold value or at most $10^{-4}$ S/m at an upper temperature threshold value.

10. The multitube X-ray emitter housing as claimed in claim 1, wherein the first electrically conductive housing portion includes at least one of flint glass, proceri, silicon nitride, silicon carbide, zirconia, silicon or a doped material.

11. The multitube X-ray emitter housing as claimed in claim 1, further comprising:
 a first bushing configured to accommodate a first high-voltage contact, wherein
  the first bushing includes an attaching device configured to detachably couple a first high-voltage electrode to the first high-voltage contact, and
  the attaching device includes at least one of a clamping device, a screwing device or a plug-in device.

12. The multitube X-ray emitter housing as claimed in claim 11, wherein the first bushing includes an insulating grommet to electrically insulate the first high-voltage electrode from the first bushing.

13. The multitube X-ray emitter housing as claimed in claim 12, further comprising:
 a seal configured to seal the housing, the seal arranged between the first bushing and the housing.

14. The multitube X-ray emitter housing as claimed in claim 11, wherein the first bushing includes a material with a temperature-dependent electrical conductivity.

15. The multitube X-ray emitter housing as claimed in claim 11, further comprising:
 a seal configured to seal the housing, the seal arranged between the first bushing and the housing.

16. A multitube X-ray source, comprising:
 at least one multitube X-ray emitter housing as claimed in claim 1; and
 a plurality of X-ray tubes, each of the plurality of X-ray tubes including a vacuum housing with a cathode and an anode to generate X-rays, wherein
  an acceleration path for emitted electrons is provided between the cathode and the anode, and
  the anodes or the cathodes form high-voltage electrodes and are, in each case, coupled to the plurality of high-voltage contacts.

17. The multitube X-ray source as claimed in claim 16, wherein at least one of the plurality of X-ray tubes protrudes from the housing such that X-rays generated at least one anode propagate away from the housing.

18. The multitube X-ray source as claimed in claim 16, wherein a distance between the first electrically conductive housing portion and one of the plurality of X-ray tubes is less than an intermediate insulation distance along the electrically insulating cooling medium.

19. An X-ray device, comprising:
 a multitube X-ray source as claimed in claim 16; and
 an X-ray detector.

20. A computed tomography device, comprising:
 a plurality of X-ray devices as claimed in claim 19, wherein
  housings of multitube X-ray emitter housings of the plurality of X-ray devices are arc-shaped,
  the housings cover at least 180°, and
  a distance between adjacent ones of the plurality of X-ray tubes is equidistant.

* * * * *